United States Patent [19]

Munck et al.

[11] 4,421,772

[45] Dec. 20, 1983

[54] METHOD FOR IDENTIFYING BOTANICAL COMPONENT PARTS OF GROUND SEEDS

[75] Inventors: Lars Munck, Helsingor; Gregory C. Gibbons, Virum; Carol Feil, Greve Strand, all of Denmark

[73] Assignee: De Forenede Bryggerier A/S, Copenhagen, Denmark

[21] Appl. No.: 296,612

[22] Filed: Aug. 26, 1981

Related U.S. Application Data

[63] Continuation of Ser. No. 88,231, Oct. 25, 1979, abandoned.

[30] Foreign Application Priority Data

Nov. 1, 1978 [SE] Sweden .................. 7811307

[51] Int. Cl.$^3$ ............... G01N 21/64; G01N 33/02; G01J 3/30
[52] U.S. Cl. ................ 426/231; 241/9; 250/461.1; 356/317; 356/433; 426/240; 426/248
[58] Field of Search ........... 426/231, 237, 240, 248, 426/242, 622; 250/458.1, 461.1; 356/317, 318, 433; 73/432 PS; 241/9, 7

[56] References Cited

U.S. PATENT DOCUMENTS 2,749,796  6/1956  Bauer .................. 426/231

OTHER PUBLICATIONS

Fulcher et al., Australian Journal of Biological Sciences, vol. 25, Feb. 1972, pp. 23–34.
Fincher, Journal of the Institute of Brewing, vol. 82, Jan.–Feb. 1976, pp. 347–349.
Lockwood, Flour Milling, published by the Henry Simon Limited, Stockport England, 1962 (pp. 15–21 and 249–262).

*Primary Examiner*—Robert A. Yoncoskie
*Assistant Examiner*—George C. Yeung
*Attorney, Agent, or Firm*—Beveridge, DeGrandi & Kline

[57] ABSTRACT

In a method for identifying one or more botanical component parts from plants, a sample of the component parts is irradiated with electromagnetic radiation within the visible and/or ultra-violet and/or X-ray range for excitation of the component parts to fluorescence which is analyzed for determining characteristic fluorescence from the component parts. For determining the relative contents of the component parts in the sample, intensity measurements are carried out on the characteristic fluorescences or the number of emitters of characteristic fluorescence is counted. For identifying starchy endosperm parts, aleurone layer parts and hull layer parts originating from seeds, in particular cereal kernels, in ground seed samples, samples are excited at approximately 275 nm, approximately 350 nm and approximately 450 nm, respectively, for obtaining characteristic fluorescence at approximately 330 nm from the starchy endosperm parts, at approximately 420/470 nm from the aleurone layer parts, and at approximately 520 nm from the hull layer parts. Characteristic X-ray fluorescence is obtained from the potassium of the starchy endosperm, phosphorus and sulfur from the aleurone layer and silica from the hull layer. For manual evaluation of the component part contents, the characteristic fluorescences of the samples are compared with color scales. Fluorescence analysis provides more reliable qualitative and quantitative analyses of botanical component parts than do visible color analyses and ash and fiber analyses and is ideally suited for the control of component part separation processes such as mill processes.

23 Claims, 17 Drawing Figures

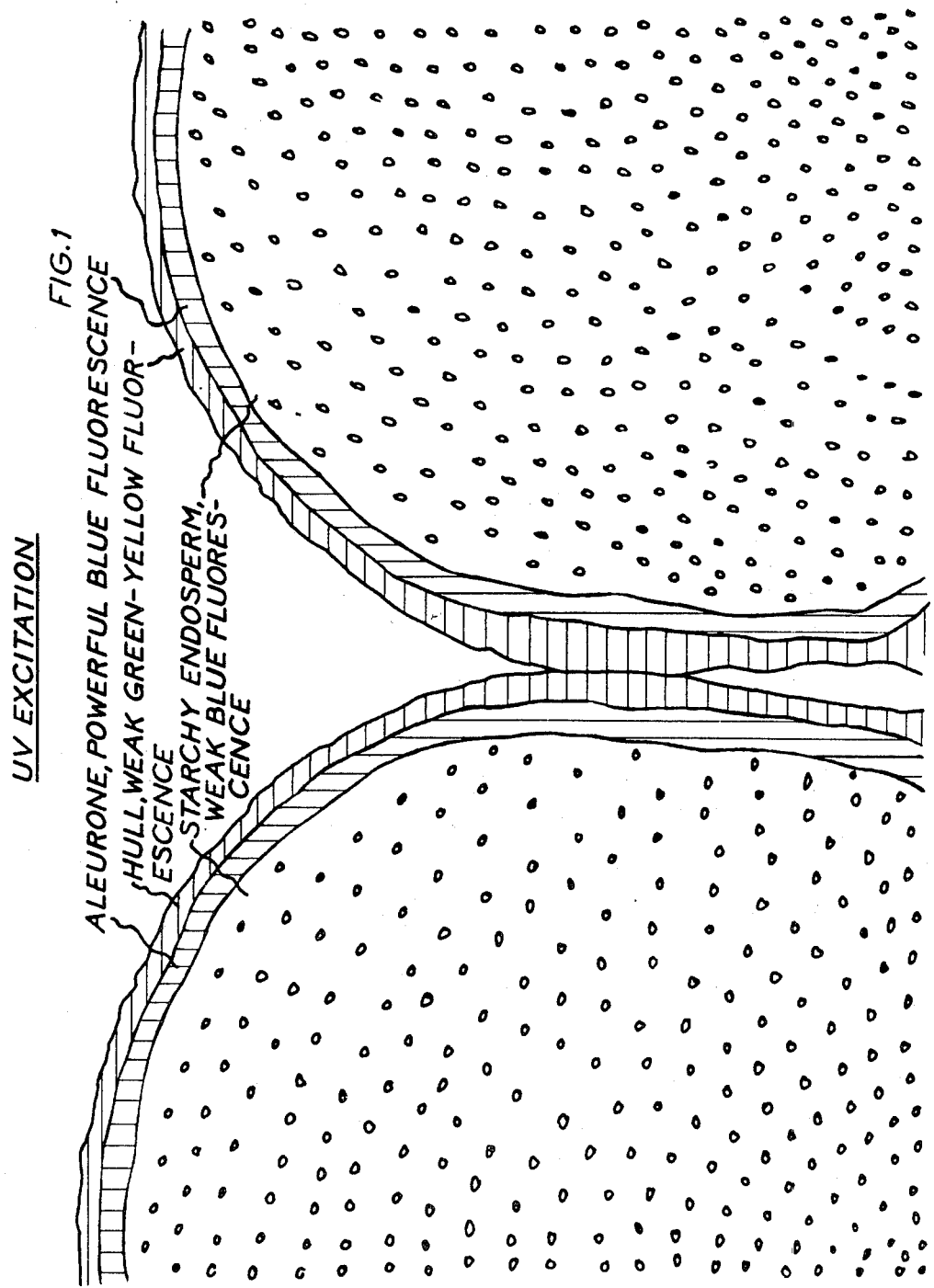

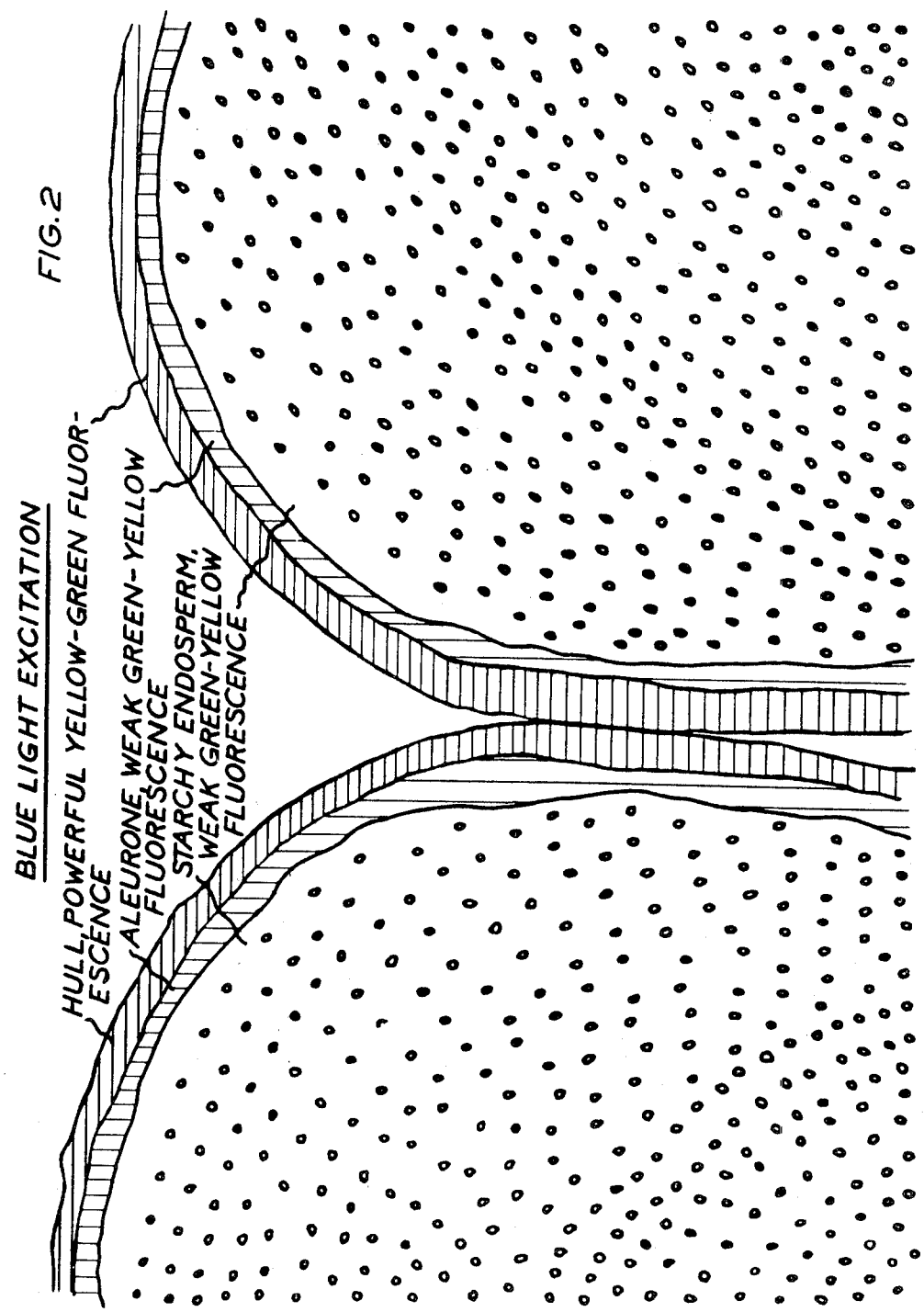

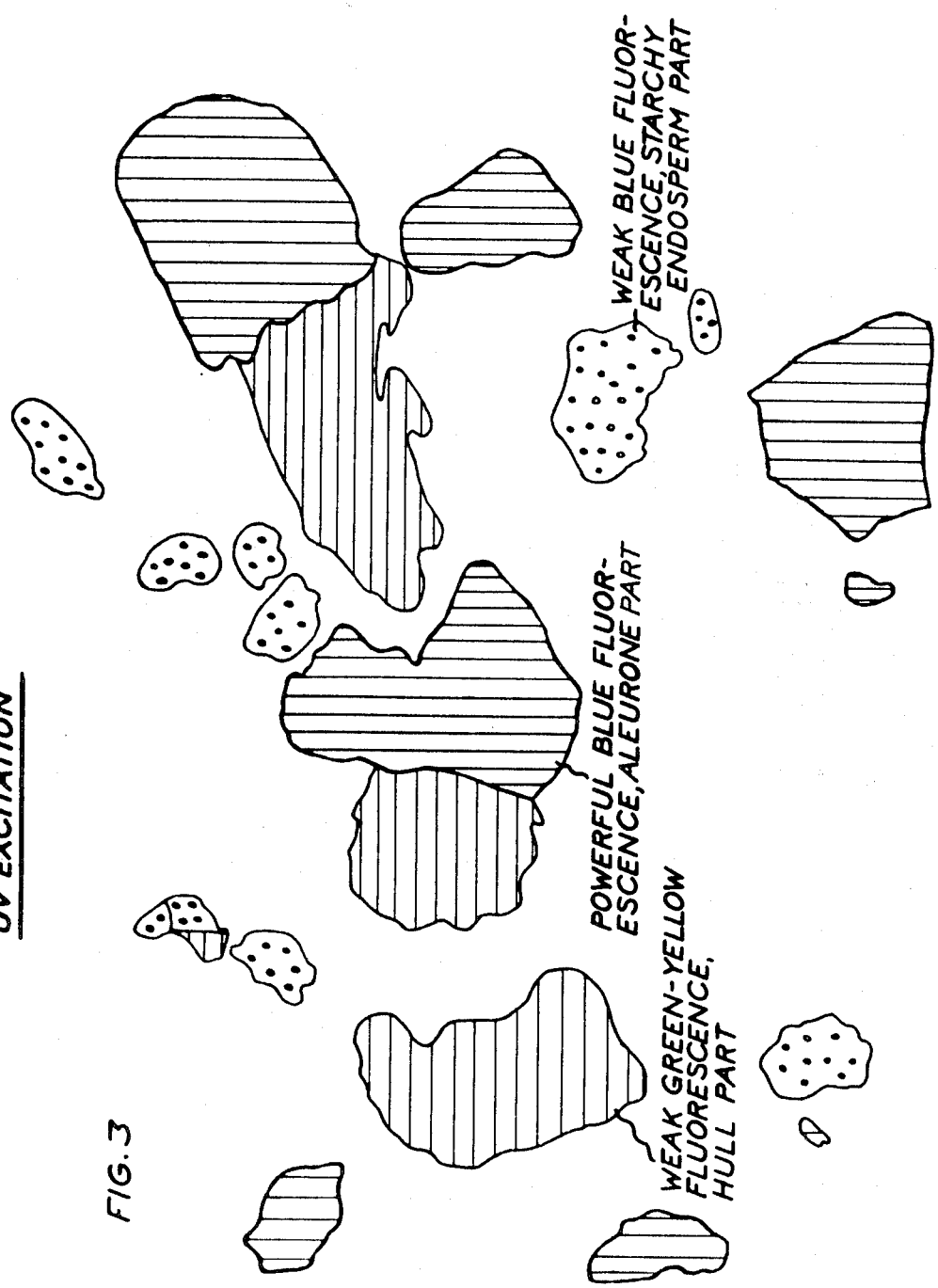

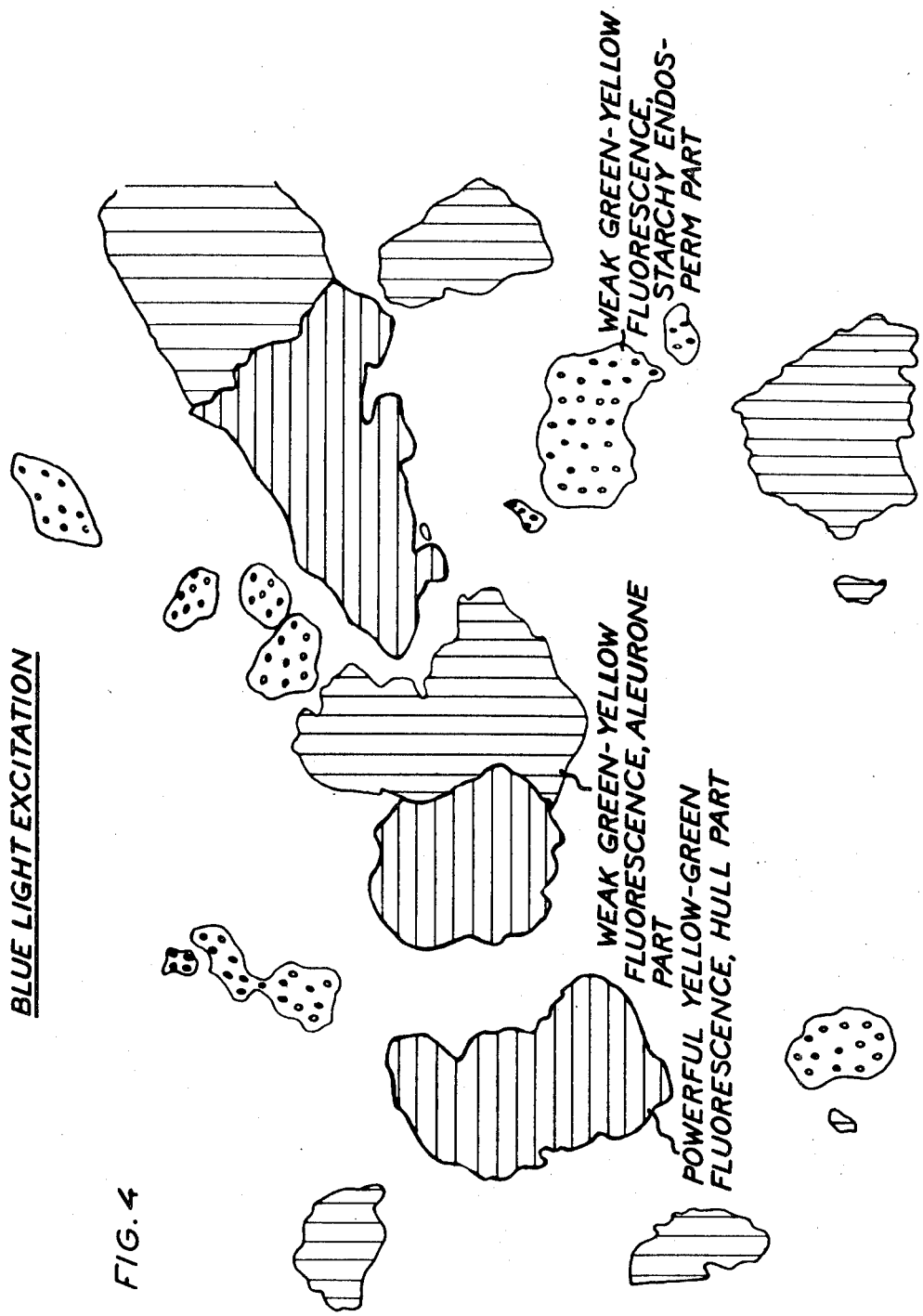

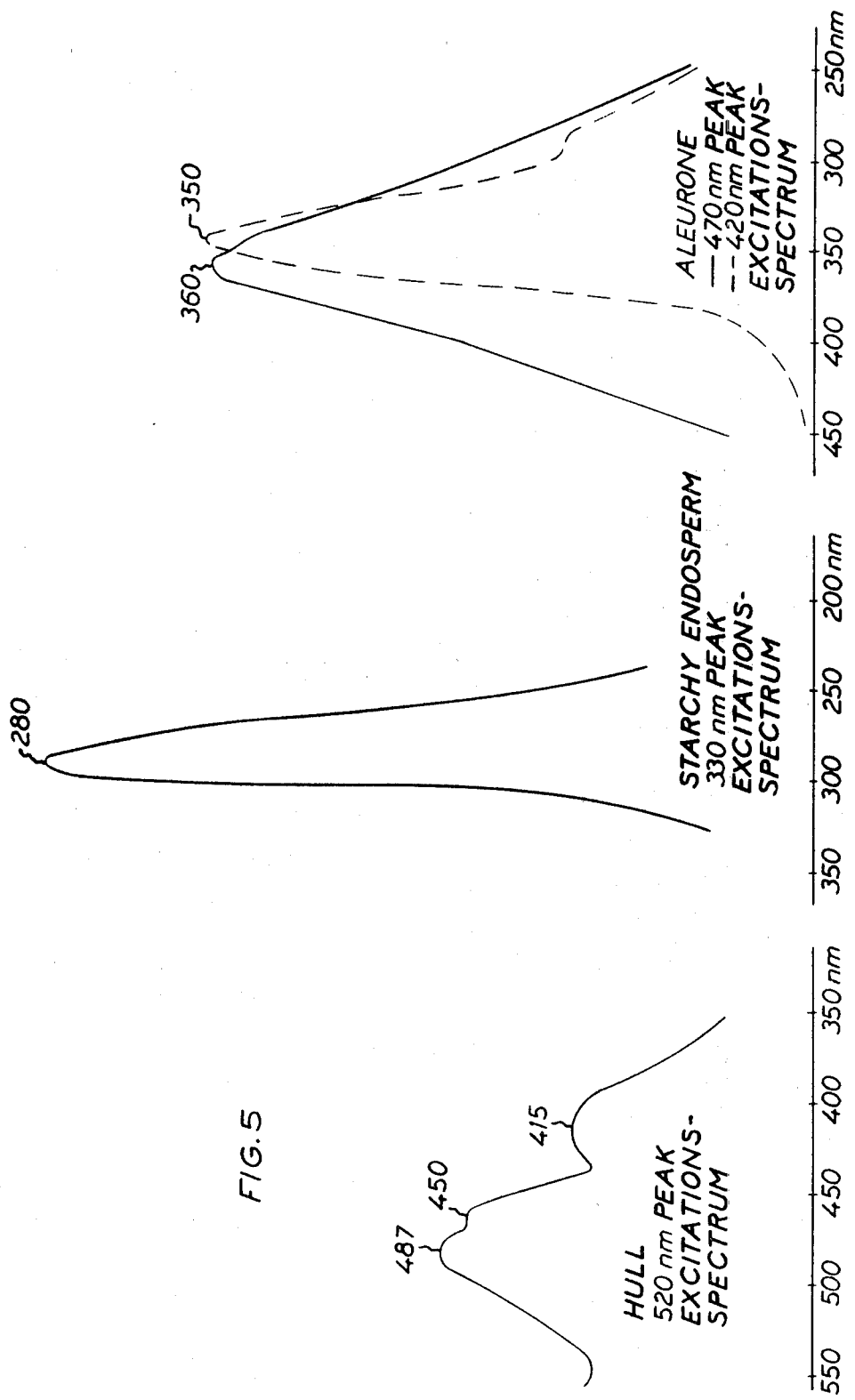

EXCITATION: 275nm

HULL FRACTION

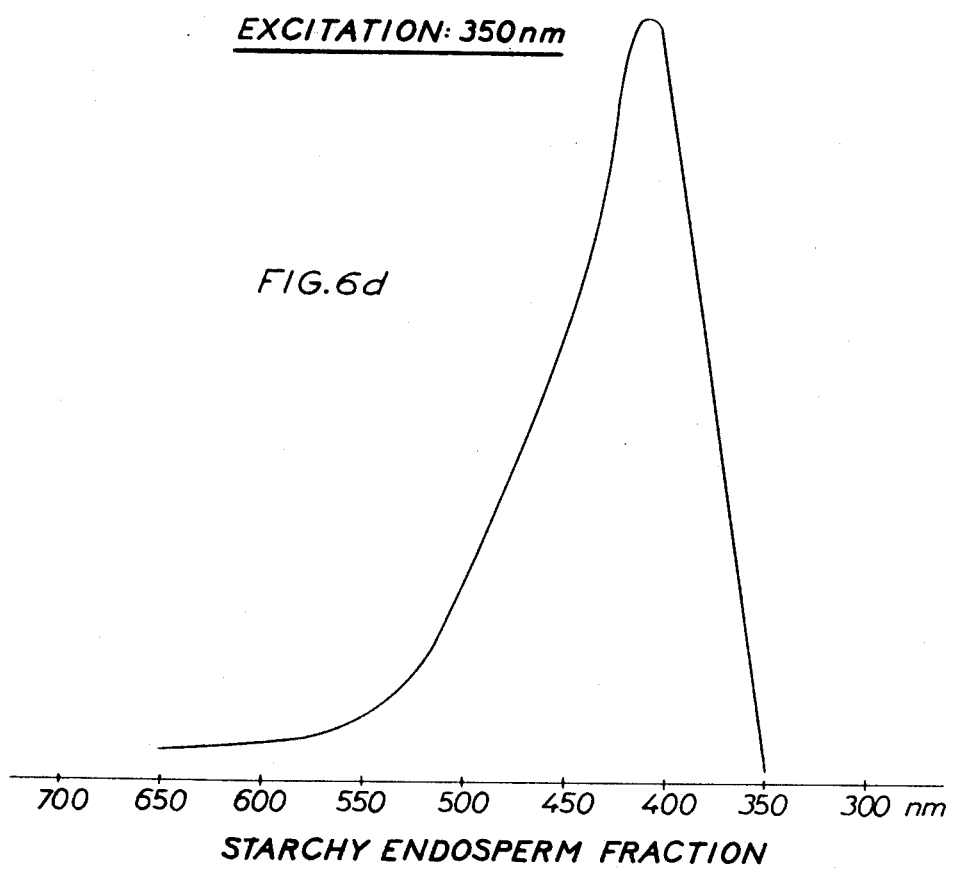

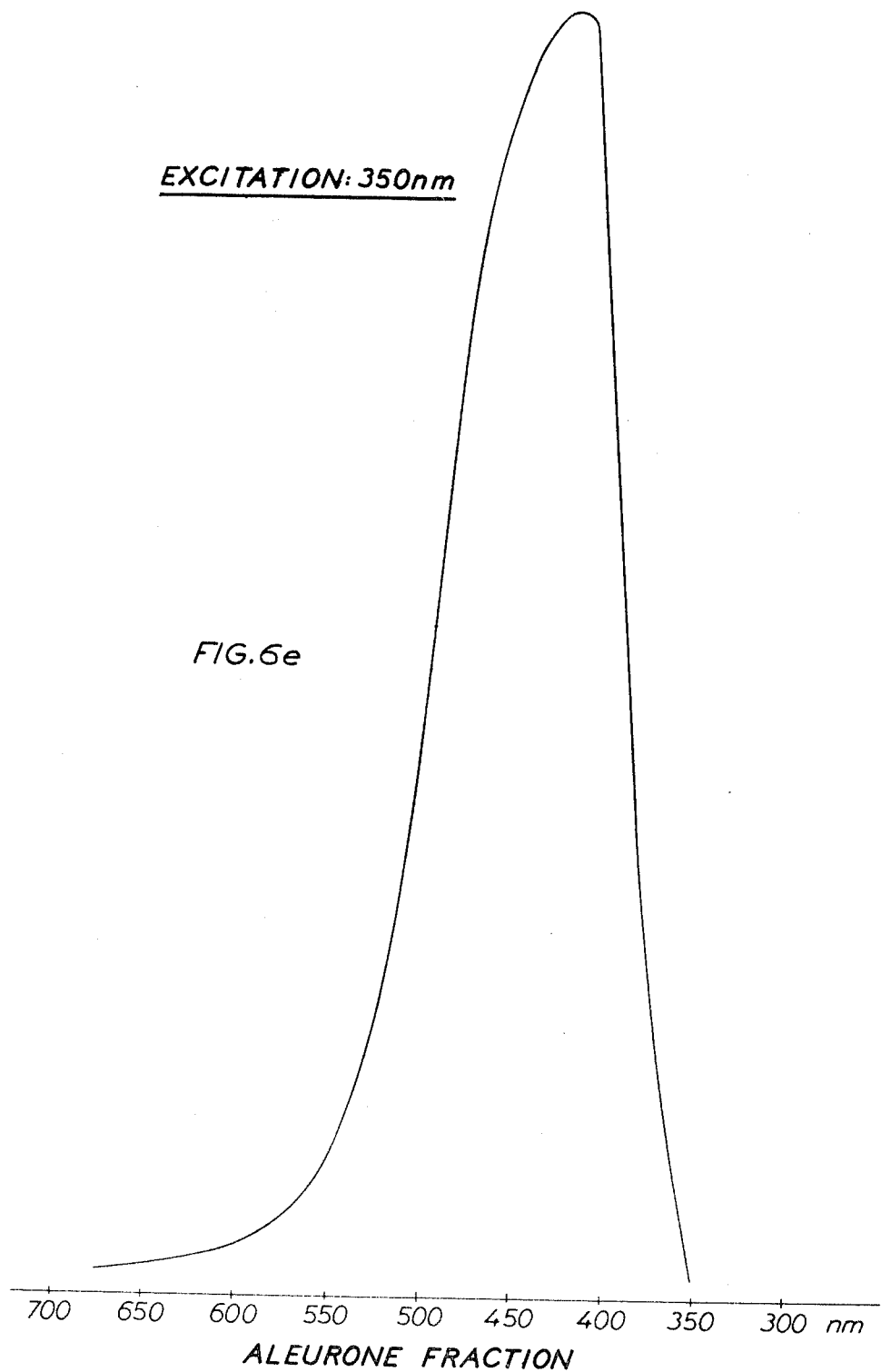
FIG.6e  EXCITATION: 350nm  ALEURONE FRACTION

EXCITATION: 450 nm

HULL FRACTION

ALEURONE FRACTION

STARCHY ENDOSPERM FRACTION

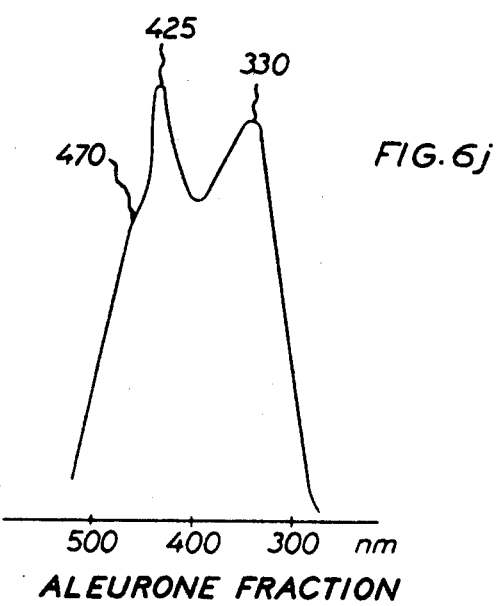
FIG. 6j ALEURONE FRACTION

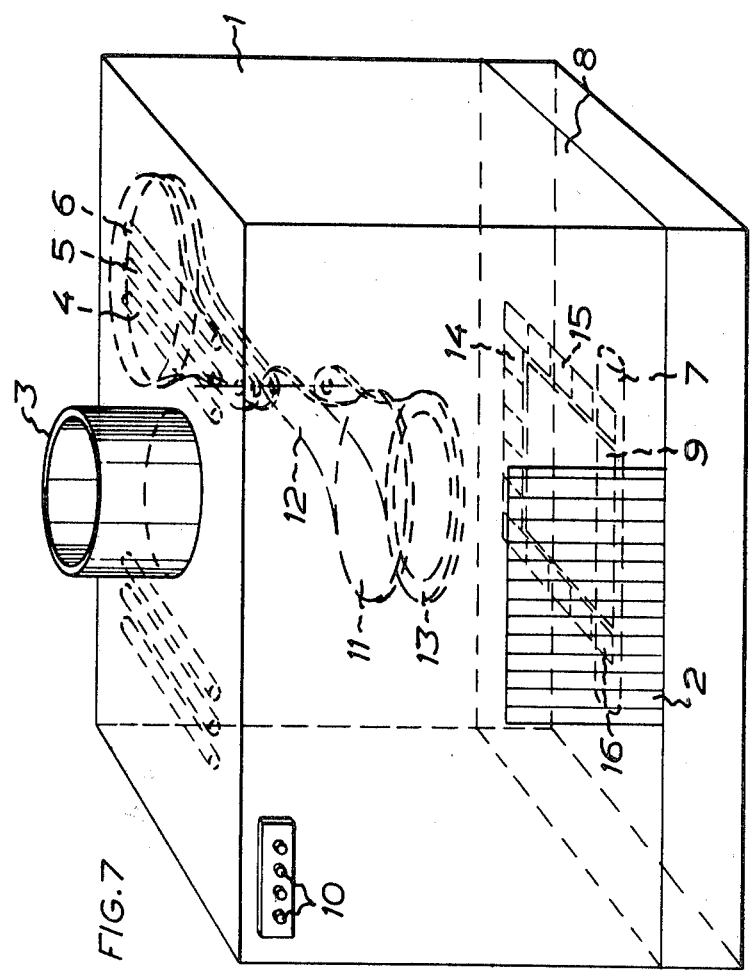

METHOD FOR IDENTIFYING BOTANICAL COMPONENT PARTS OF GROUND SEEDS

This application is a continuation of application Ser. No. 088,231, filed Oct. 25, 1979, now abandoned.

The industrial processing of kernels of seed types, cereals, such as wheat, barley, corn, rye, sorghum, rice or other seeds such as, for example, soya beans, often includes a series of steps whose aim is to separate certain of the botanical component parts of the seed from each other. These steps are carried out in a mill plant where the seed is ground and sieved in several stages in order to obtain steadily purer component part fractions with respect to other botanical component parts. The conventional botanical seed or kernel component parts of cereals topical for separation are (a) the starchy endosperm which consists of the endosperm minus the aleurone layer, (b) the germ, (c) the aleurone layer and (d) the hull layer which layers are usually classified under the name bran. The starchy endosperm consists of cells with thin cell walls containing starch particles in a matrix of protein, and forms the main source of the major end product of the mill industry, the flour. The hull layer and aleurone layer fractions, as well as the germ fractions, may each best be taken care of in their optimum manner, for example as fodder or as an additive in determined amounts to the flour, depending upon the nature of the raw materials or product. Recent insights into the importance of diet fibers have directed interest towards the hull fraction in its property as a source of fibers, as well as towards the utilization of the high mineral and vitamin content of the aleurone fraction.

The grinding and sieving devices of the conventional mill process are based on the different hardnesses and densities of the hull layer, the aleurone layer and the starchy endosperm, these devices being provided for the breaking down of the seeds to smaller and smaller particles and for classification of these particles according to size and density in several different fractions which contain varying amounts of the starchy endosperm, aleurone and hull parts. As was mentioned above, the main aim is that the mill process give steadily purer (that is to say steadily freer of other component parts) component part fractions, and the grinding devices and sieves are adjusted for this purpose.

The analysis methods necessary for assessing the composition of the fractions with respect to the above-mentioned botanical component parts for product control and for ascertaining the capacity of the grinding and sieving devices (and other mill devices which affect the fraction composition) to carry out their task in the light of the above purposes are, however, very time-consuming and unreliable at the present time. The unreliability of these conventional analysis methods constitutes in actual fact one of the reasons for the above-mentioned striving towards purer component part fractions, even if the desired finished product is to consist of a mixture of starchy endosperm, hull and aleurone parts, since the probability of achieving a desired mixture is greater if the final fractions in the starchy endosperm, aleurone and hull lines are mixed than if intermediate products from these origins are utilized as a mixture.

The conventional analysis methods are based on color determination in visible light, on ash and fiber determination and on sieve analyses. In color determination in visible light, an assessment is made of the degree of which a ground seed sample deviates in color from that of an ideal sample, and, in particular, the color deviation of a flour sample from the white color of ideal bakery flour, the color deviation being possibly caused by the presence of hull component parts in flour, these being brown in color, int. al. depending upon included carotenoids etc.

The color analysis may be qualitatively unreliable, since impurities which do not consist of hull component parts may very well give rise to a color similar to that of the hull. It has, thus, proved that mill equipment of metal and rubber shed metal and rubber particles which may discolor the flour such that it gives the impression of containing hull particles. This apart, such a color analysis on flour samples or hull samples gives no indication whatsoever as to the presence of aleurone layer particles or particle parts, since these are colorless in visible light.

Ash and fiber analysis according to, for example, the Weende method also provides insufficient and incomplete information as to the content, in a ground seed sample, of each respective seed component part. The explanation for this is that, while the major part of ashy components is present in the aleurone layer and the major part of the fibers occurs in the hull layer, all of the seed component parts now under discussion contain both ashy components and fibers. In consequence, the analysis result of a ground seed sample, as regards contents of fiber and ash, cannot reliably correlate the ash and fiber to the aleurone layer and hull layer, respectively. Hence, high content of, for example, ash in a sample may very well depend upon an enrichment of hull instead of aleurone in the sample.

The aim of sieve analysis is to divide up, according to size, the particles in a ground seed sample, this analysis failing, however, to give any information as to the component parts from which the separate particles have their origin.

Thus, it will be appreciated that conclusions based on color, ash and fiber determination, and on sieve analyses, for an optimation of the separation of the botanical components involved, may give rise to highly erroneous mill settings and product specifications. Moreover, it might be mentioned that sieve analyses and, in particular, ash and fiber determinations, are extremely time-consuming.

The major aspect of the present invention is to realize a method and an apparatus which will master the above-mentioned problems as regards unreliable and incomplete product analyses and mill control methods and which will bring about the possibility of reliably identifying botanical component parts such as hull layer, aleurone layer and starchy endosperm component parts in entire seeds or kernels and in ground seeds or kernels and, thereby, the possibility of following these component parts during the mill process. As a corollary to this aspect, a further aim of the present invention is to utilize the above-mentioned possibilities for manual and/or automatic control of a mill process.

To this end, the component parts are, according to the method of the present invention, irradiated with fluorescence-imparting electromagnetic radiation, whereupon the fluorescence or fluorescences emitted from the above-mentioned component parts are analyzed for determining either a fluorescence emission characteristic of the component parts and, possibly, the intensity of this emission; or the absence of such a characteristic fluorescence emission.

Furthermore, the apparatus for carrying out this method comprises a container disposed for receiving the sample at a sample receptacle point in the container, an orifice in a container wall for viewing the sample, one or more devices for excitation of the component parts to fluorescence, means for analysis of this fluorescence for determining characteristic fluorescence from the component parts, and possibly means for determining the intensity of the characteristic fluorescence or fluorescences for determining the relative content, in the sample, of the component parts.

The nature of the present invention and its aspects will be more readily understood from the following brief description of the accompanying drawings, and discussion relating thereto.

In the accompanying drawings:

FIGS. 1 and 2 illustrate color photographs of the same wheat kernel section on illumination with different excitation light;

FIGS. 3 and 4 illustrate color photographs of ground wheat kernel particles on illumination with the same excitation lights, respectively, as in FIGS. 1 and 2;

FIG. 5 is an excitation curve;

FIGS. 6a–6j are emission curves;

FIG. 7 is a schematic illustration of an apparatus according to the invention for identification and assessment of the amount of biological component parts in ground kernels or seeds.

Figure 6A:
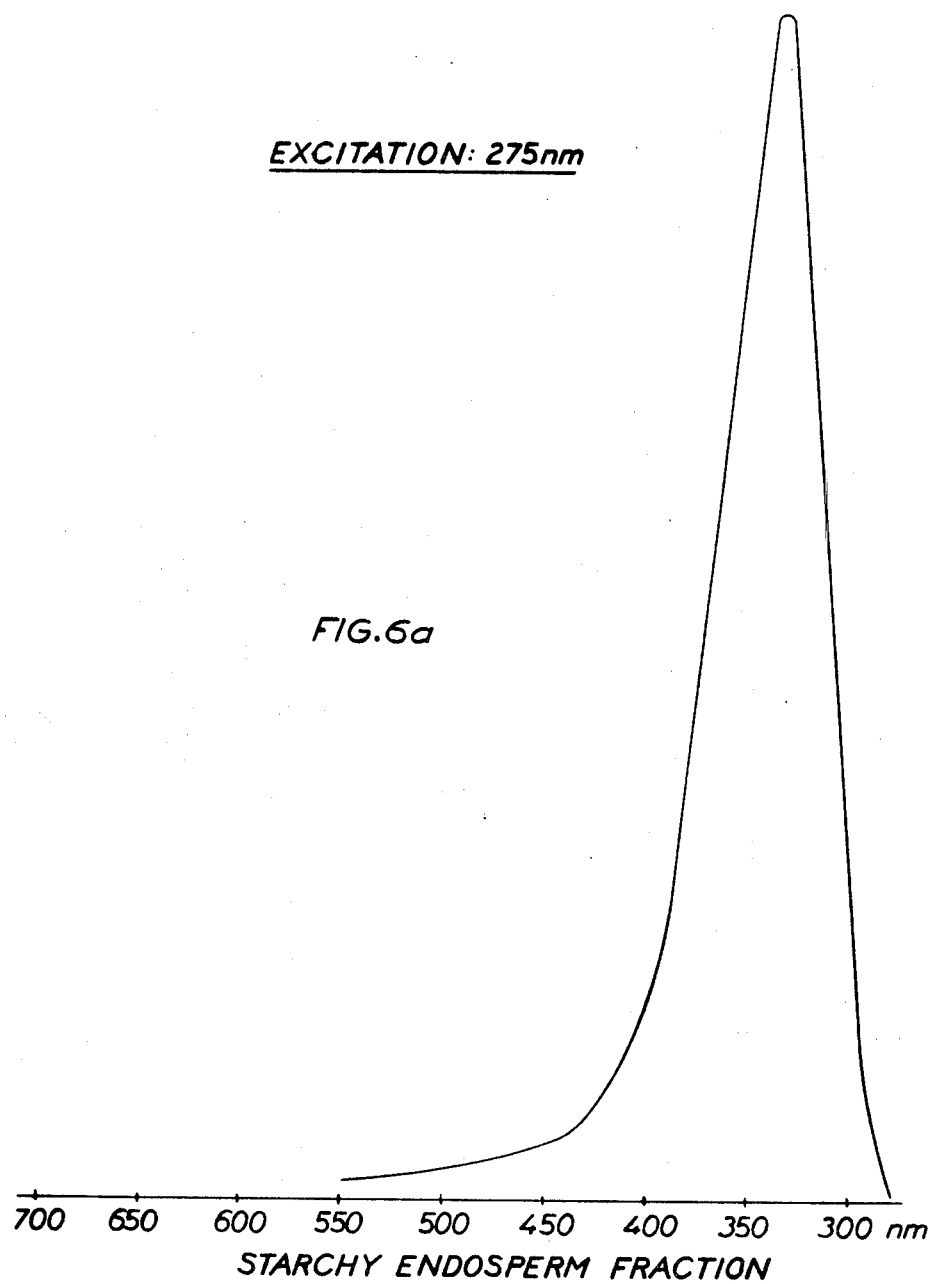
Figure 6B:
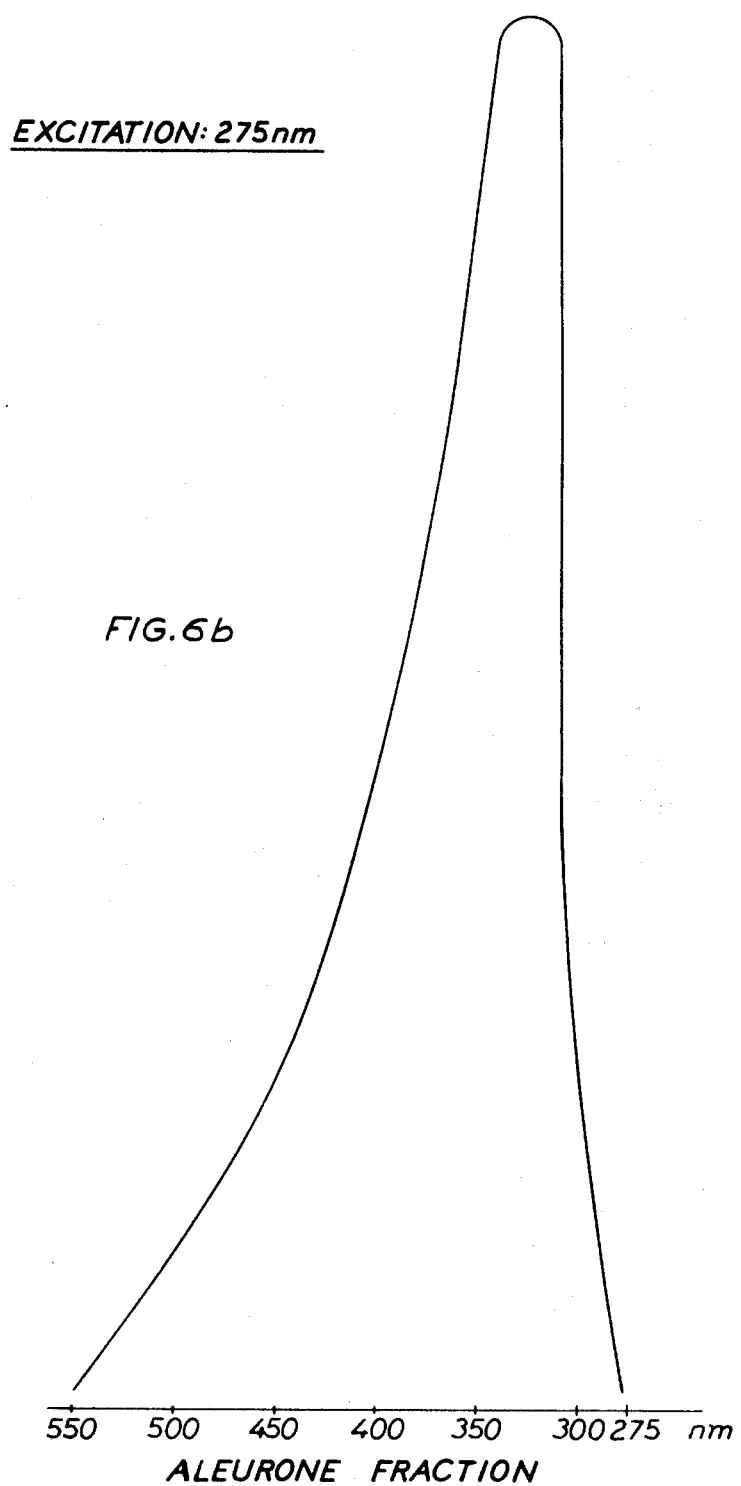
Figure 6C:
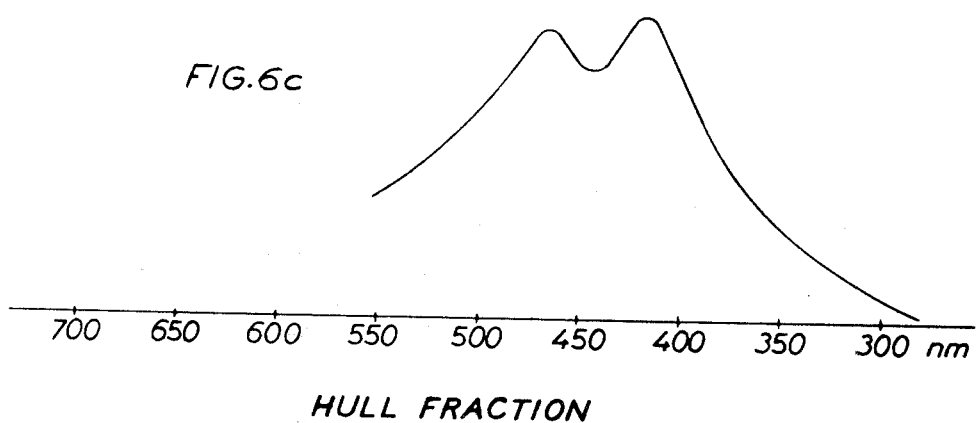
Figure 6F:
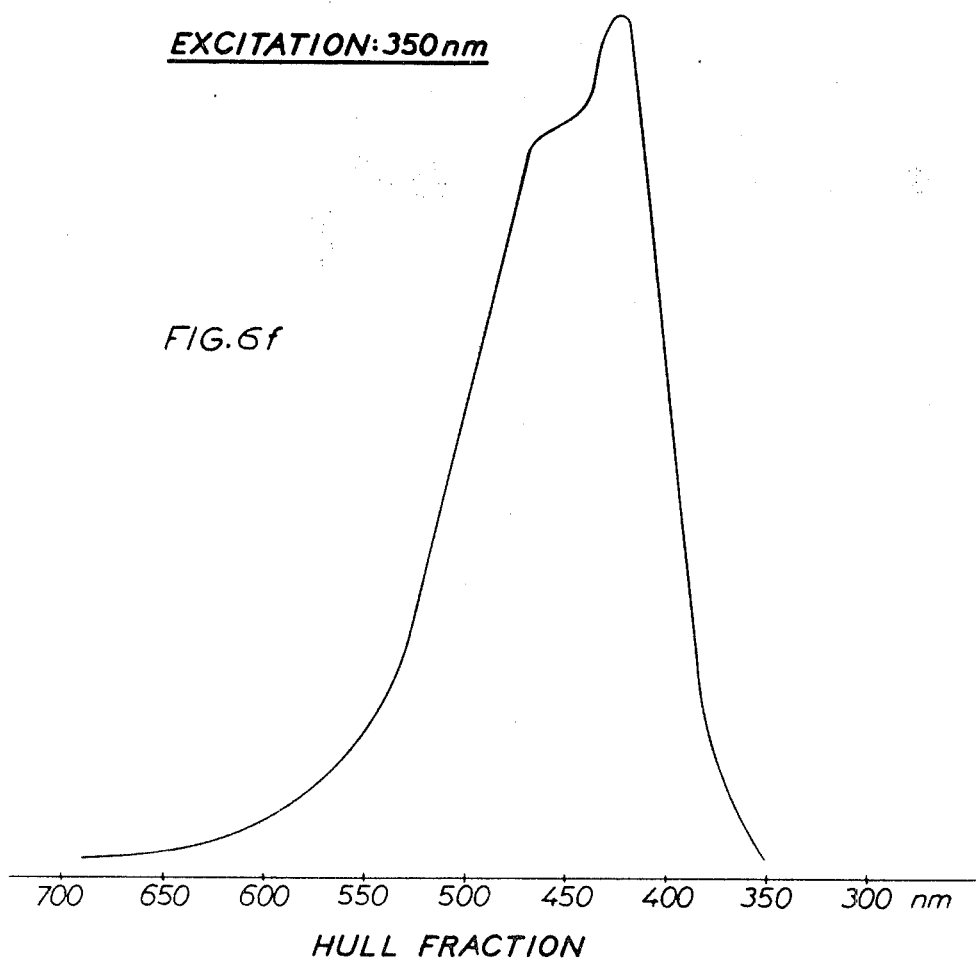
Figure 6G:
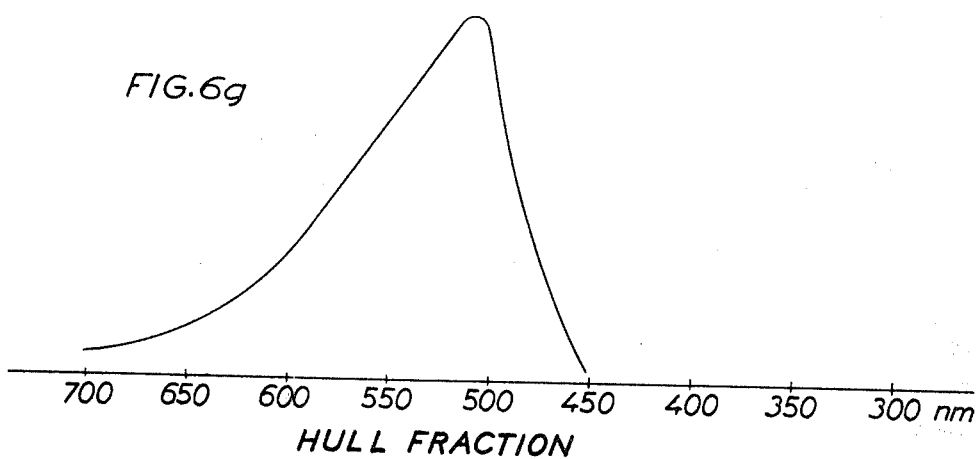
Figure 6H:
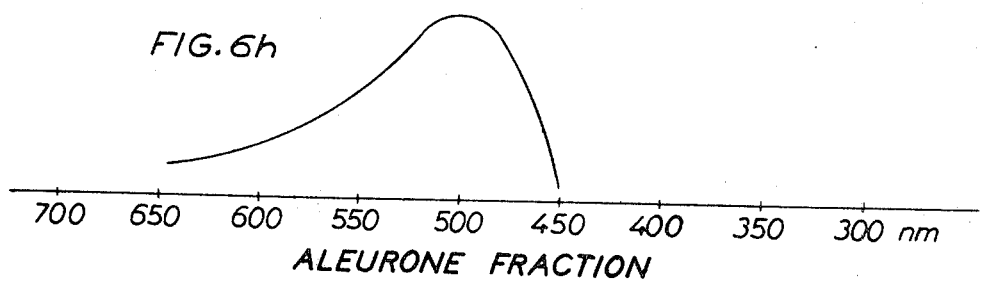
Figure 6I:
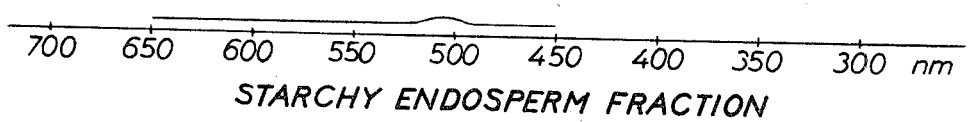

Early on in research work for suitable analysis methods for attaining the established goals, interest was concentrated on fluorimetry, partially induced by earlier findings which revealed autofluorescence from the aleurone layer, hull layer and starchy endosperm cell walls of grain seed on irradiation with incident UV-light. (Aust. J. Biol. Sci. 1972, 25, 23–24, and J. Inst. Brew, Vol 82, 347–349).

Different wheat kernels cast in plastics and in transverse section with highly polished section surfaces were illuminated in a fluorescence microscope with incident ultra-violet light. Under observation in the microscope, a circumferential layer in each kernel fluoresced with a distinct intensive blue light, it being established that this layer was the aleurone layer. It should be emphasized that this blue light was very distinct and could be clearly differentiated from the very faint, damped blue light from the body lying within the aleurone layer, it being possible to relate this faint, damped blue light, on magnification, to the cell walls of the starchy endosperm. This distinct intensive blue light could also be distinguished from the faint, damped green-yellow light emanating from the hull layer lying outside the aleurone layer. On illumination of these wheat kernels with incident blue light, the hull layer located outside the aleurone layer fluoresced with an intensive yellow-green color which clearly distinguished the hull layer from the aleurone layer and starchy endosperm, both exhibiting a very pale, damped green-yellow color. These results of the microscope examination are illustrated in FIGS. 1 and 2 which are drawings from color photographs taken, through the microscope, of adjacent parts of two wheat kernels in cross-section, under illumination with UV-light and blue light, respectively. It may be noted in this context that different UV-light sources and blue light sources, as well as filters permeable to such UV-light and blue light (excitation filters) and filters for the light emitted by the kernels (emission filters) were tested, no problems arising with respect to the unambiguous identification of starchy endosperm, hull and aleurone layers with the help of the autofluorescence of these kernel component parts. The autofluorescence was characteristic and unambiguous for these kernel component parts, although the colors could vary in dependence upon the light and filter combinations, from blue to violet for the aleurone layer and green to yellow for the hull layer. The bluish autofluorescence of the aleurone layer and the greenish autofluorescence of the hull layer appeared separately even under illumination of the wheat kernels with almost UV-light, which fluorescence colors could be made more distinct by the placing of suitable blue and yellow filters, respectively, in the path of the light emitted from the seed.

Having thus established characteristic, intensive autofluorescence from the aleurone and hull layers and the absence of intensive autofluorescence from the starchy endosperm, a grinding of the kernels was then carried out, the grounds being placed under a microscope. The microscope image reflected the same fluorescence colors on the ground kernel particles as were obtained in the above-mentioned observation of the kernel section surfaces. The expression—the same fluorescence colors—means, on irradiation of the ground samples with the same excitation light as that used with the kernel section surfaces and possibly on utilization of the same emission filters, that certain of the particles had, in their entirety, the same intensive, distinct blue color as the aleurone layer in the section test, that certain of the particles had, in their entirety, the same intensive, yellow-green fluorescence color as the hull layer in the section test, that certain of the particles lacked the intensive blue and yellow-green colors, respectively, characteristic of the aleurone layer and hull layer, and exhibited the pale blue and pale green-yellow color, which, in the section surfaces, could be related to the starchy endosperm; that certain of the particles presented a portion which fluoresced in the intensive blue color characteristic of the aleurone layer and a portion which fluoresced in the intensive yellow-green color characteristic of the hull layer; and that certain of the particles displayed demarcated regions exhibiting both the above-described intensive "aleurone fluorescence color" and the above-described intensive "hull fluorescence color" as well as the above-described pale "starchy endosperm color". The particles from the starchy endosperm were also identified with the assistance of polarized light under which starchy materials become manifest. The aleurone and hull portions almost completely lack starchy material and do not, therefore, follow this behavior. FIGS. 3 and 4 show drawings of color photographs which were taken of the microscope pictures of one and the same ground kernel sample on ultraviolet excitation (FIG. 3) and blue light excitation (FIG. 4), respectively, the black regions in FIG. 3 having the same intensive blue fluorescence as the black aleurone layer in FIG. 1, and the black regions in FIG. 4 having the same intensive yellow-green fluorescence as the black hull layer in FIG. 2. The striped and dotted regions in FIG. 3 and FIG. 4, respectively, had the same colors in blue light and UV-light excitation as the striped and dotted kernel component parts in FIGS. 1 and 2. These colors have been described in conjunction with the discussion on FIGS. 1 and 2.

The important information which could and can be gained from these pictures is, on the one hand, that it is possible to identify visually whether particles or particle portions belong to the aleurone layer, the hull layer or the starchy endosperm on irradiation with UV- and blue light, respectively; and, that the fluorescence colors from component parts deriving from the aleurone and hull layers do not influence adjacent particles or particle portions such that the color of these particles or particle portions is lost or suppressed.

The above-described excitation and emission results could be obtained from cereal kernels other than wheat kernels and, in general, from seeds of both monocotelydones and dicotelydones.

Once it had, thus, been established that it was possible with the aid of the eye, suitable sources of light and/or emission filters and excitation filters, to identify unambiguously or analyze qualitatively particles or particle portions which derive from the aleurone, hull and starchy endosperm component parts in seeds and kernels, measures were taken to ascertain whether these qualitative analysis results could be transformed into a quantitative analysis method. Ground wheat kernel samples suspended in glycerine were placed in a spectro-fluorimeter which was of the Jasco FP 550 type and was connected to a printer, and were scanned with emission monochromator settings from 300 nm to 700 nm on varying excitation wavelengths. The samples were taken from final steps of the flour line, aleurone line and hull line, respectively, in a mill plant. The samples were placed in the fluorimeter at an angle of 30° with respect to the excitation light for the purposes of preventing the excitation light and emission light from mixing. It proved that, on excitation of the flour sample with light at 275 nm, an emission or fluorescence intensity peak was obtained at 330 nm, which closely corresponds to the fluorescence intensity peak, at this excitation wavelength, of the protein amino acids tyrosine and tryptophane. On excitation of aleurone samples with light at 350 nm, an emission or fluorescence intensity peak was obtained at 420 and 470 nm, which closely corresponds to the fluorescence intensity peak, at this excitation wavelength, of ferulic acid. On excitation of a hull sample with light at 450 nm, an emission or fluorescence intensity peak was obtained at 520 nm. In order to establish the excitation wavelength or lengths which give maximum fluorescence intensity at 330 nm, 425 nm, 475 nm and 520 nm fluorescences, the emission monochromator was held at these fluorescence wavelengths and each respective sample was scanned with the excitation monochromator at wavelengths of less than the respective fluorescence wavelength. It proved that a 280 nm excitation light gave maximum fluorescence intensity of the fluorescence of the flour sample at 330 nm, that 350 nm excitation light gave maximum fluorescence intensity of the fluorescence of the aleurone samples at 420 nm and an excitation light of 360 nm gave maximum fluorescence intensity for the fluorescence of the aleurone samples at 470 nm. Finally, excitation light at 415, 450 and 487 nm gave maximum fluorescence intensity of the fluorescence of the hull sample at 520 nm. These results are illustrated in FIG. 5.

In the application of the German color theory according to DIN 6164, by means of which it is possible to correlate the sensitivity of the eye to different colors with the sensitivity of a photomultiplier tube included in the spectrofluorimeter, it could be established that the peaks, obtained with the spectrofluorimeter, at 330 nm, 425 and 470 nm and 520 nm to the eye appeared to be colorless, blue-violet and yellow-green, respectively, such that the spectrofluorimeter values back up the results from the microscope observations.

Once the establishment was made that the hull samples, aleurone samples and starchy endosperm samples each had at least one characteristic fluorescence (namely: the hull samples 520 nm fluorescence at 487, 450 and 415 nm excitation; the aleurone samples 420 nm and 470 nm fluorescence at 350 nm and 360 nm excitation, respectively; and the starchy endosperm samples 330 nm fluorescence at 275 nm excitation), a test was carried out of the capacity of these fluorescences to differentiate the kernel component parts hull layer, aleurone layer and starchy endosperm from each other. FIGS. 6a–6j represent the fluorescence intensity curves, or emission curves, obtained in such a test of one flour sample, one aleurone sample and one hull sample, the samples being each excited with light at 275 nm, 350 nm and 450 nm. The above-mentioned printer connected to the Jasco FP 550 spectrofluorimeter had the same amplification factor in all of the experiments.

The tests revealed, as shown by the curves in FIGS. 6a–6j, that an excitation at 275 nm (FIGS. 6a–6c) gave rise to considerable fluorescence intensity at approximately 330 nm also from the aleurone sample which had, however, a much broader peak than the flour sample. This may be explained partly by the relatively high protein content of the aleurone layer and partly by adulteration of the aleurone sample with starchy endosperm particles. When the sample amounts were reduced, it was possible to distinguish starchy endosperm parts and aleurone layer parts, cf. FIG. 6j, represented by emission at 330 nm and 425 nm, respectively, and 470 nm. There was no appreciable fluorescence intensity at 330 nm from the hull sample on excitation at 275 nm. 350 nm excitation (FIGS. 6d–6f) gave rise to considerable fluorescence intensity at approximately 450 nm from the aleurone samples. This fluorescence intensity could also be identified in the starchy endosperm and hull samples, which may be explained by the ferulic acid content of the starchy endosperm and of the hull. 450 nm (FIGS. 6g–6i) excitation gave rise to considerable fluorescence intensity at 520 nm from the hull samples and minor fluorescence intensity at 520 nm from the aleurone samples. The flour samples exhibited as good as no fluorescence intensity at 520 nm.

The amounts of the hull, aleurone and starchy endosperm samples taken from the above-mentioned final stages in the hull line, aleurone line and starchy endosperm line were increased in several steps and the fluorescence intensities of these increased sample amounts were determined at the following excitation/emission wavelengths: 275 nm/330 nm, 350 nm/425 nm and 450 nm/550 nm. It was ascertained that increased sample amounts gave rise to increased fluorescence intensities, although certain intensity leveling-out effects could be noted at higher sample amounts, which may be explained by the concealment of fluorescent particles in too large sample amounts. Table 1 represents a series of experiments with increased sample amounts. The same Table also reproduces typical tendency results of fluorescence intensity determinations on samples which were obtained by a mixture of flour fraction, aleurone fraction and hull fraction. The intensity determinations of the fluorescence from mixtures of the flour fraction and aleurone fraction showed conclusively that the 330 nm emission at 275 nm excitation may unequivocally be related to the starchy endosperm, since an increased weight ratio of starchy endosperm fraction to aleurone fraction gave increased fluoroescence intensity. It was also shown conclusively that the 550 nm emission at 450 nm excitation may be related to the hull.

It could furthermore be ascertained that the starchy endosperm samples mixed with aleurone fraction parts and the starchy endosperm samples mixed with hull fraction parts exhibited less fluorescence intensity than the starchy endosperm fraction sample when the starchy endosperm samples and the purer starchy endosperm fraction samples had the same weight and were irradiated at 275 nm, the emission monochromator being set at 330 nm. This intensity-reduction may be explained by the fact that the emission at 330 nm from the four sample is a source of excitation for the aleurone fraction part and, thus, does not escape from the mixture sample; and that the 425 nm and 470 nm emission of the aleurone fraction part, excited at 330 nm, is an excitation source for the hull fraction part.

TABLE 1

| flour fraction | aleurone fraction | hull fraction | 275 330 | 350 425 | 450 excitation (nm) 550 emission (nm) |
|---|---|---|---|---|---|
| sample amounts (mg) | | | intensity values | | |
| 10 | | | 600 | | |
| 20 | | | 980 | | |
| 30 | | | 1100 | | |
| 40 | | | 1400 | | |
| | 10 | | | 95 | |
| | 20 | | | 150 | |
| | 30 | | | 160 | |
| | 40 | | | 160 | |
| | | 10 | | | 9 |
| | | 20 | | | 14 |
| | | 30 | | | 19 |
| | | 40 | | | 43 |
| 10 | 40 | | 292 | 160 | |
| 20 | 30 | | 426 | 170 | |
| 30 | 20 | | 680 | 150 | |
| 40 | 10 | | 920 | 400 | |
| 10 | | 40 | 35 | | 70 |
| 20 | | 30 | 110 | | 17 |
| 30 | | 20 | | | 23 |
| 40 | | 10 | 330 | | 11 |
| 30 | 10 | 10 | 220 | 220 | 15 |

However, these investigations of mixtures show, as is apparent from the above Table, that the adulteration of the flour fraction sample with hull layer and aleurone layer parts may be quantitatively determined in a simple manner, this quantitative determination being carried out with the assistance of intensity values from known mixtures (that is to say mixtures with known weight ratios of flour/aleurone plus hull). It should, nonetheless, be emphasized that calculation methods, preferably computerbased, for determining the content of different fluorescent substances in a mixture of such substances on illumination of the mixtures with different excitation wavelengths, are available to persons skilled in the art, these calculation methods being applicable to mixtures of seed or kernel component parts.

Another method according to the invention of determining absolute amounts of starchy endosperm parts, aleurone layer parts and hull layer parts is image analysis of the discrete particles of samples, carried out by means of an apparatus according to the invention, which consists of a conventional image analyzer, coupled to a fluorescence microscope having means for excitation and emission of radiation at or close to the wavelengths determined in accordance with the above by means of the spectrofluorimeter. Image analyzers are most often adjustable on different gray scale values, the different, above-described fluorescences at varying excitation wavelengths or at one excitation wavelength being sensed with the assistance of different gray scale values and related to the seed or kernel particles or particle parts which give rise to these fluorescence colors. According to Table II, samples were analyzed from the hull line, aleurone line and flour line, respectively, of a mill plant, in a Quantimet 720 (Cambridge Instrument) image analyzer whose TV camera, provided with a plumbicon tube, was coupled to a Reichert UNIVAR microscope under which each respective sample was illuminated with a 200 W HBO-lamp, the microscope being provided with a filter combination selected on the basis of fluorescence data (i.e. excitation at 350–450 nm and emission filters at 515–700 nm). This filter combination was selected using, as a point of departure, and fluorescence wavelengths determined by the spectrofluorimeter and was suited for detection of the fluorescence of both the hull particles and the aleurone particles. This could be confirmed in the microscope and on the TV screen. With this filter combination, the samples were illuminated at two different gray scale values, one for hull andone for hull+aleurone: The combination hull+aleurone+starchy endosperm (that is to say the entire particle surface) was measured under illumination with incandescent light. The different above-discussed samples were then intermixed in determined amounts and measured by means of the image analyser. The content of hull, aleurone and starchy endosperm, calculated on the basis of the mixture proportions, was compared with the measured values, a linear function being obtained with a correlation coefficient $r = +0.99$. Thus, as opposed to fluorescence spectrometer measurements of the fluorescence from mixed particles, it was possible, with the assistance of the image analyzer, to obtain simple linear expressions of the amounts of the botanical component parts by establishing by planimetry the surface areas of these particles by registration on different gray scale levels.

Finally, the hull fraction, aleurone fraction and flour fraction were analyzed with respect to ash, fiber and starch (please see Table II), like the above-described mixtures of these fractions. The surface areas of the hull, aleurone and starchy endosperm parts in these samples, measured with the assistance of the image analyzer, were correlated with ash, fiber and starch content determinations (please see Table II). It is apparent that hull gives a higher correlation coefficient with fiber ($+0.99$) than with ash ($+0.89$), whereas, on the contrary, the aleurone fraction gives its highest correlation coefficient with ash ($+0.98$) and a lower correlation coefficient with fiber ($+0.87$) which illustrates the great advantage of being able to calculate these botanical component parts of the seed or kernel independent of each other with great accuracy and rapidity. As was to be expected, the starchy endosperm content, calculated by means of the image analyzer (which is calculated as a difference between the total particle surface minus the hull and aleurone surfaces) is very negatively correlated with ash and fiber and very positively correlated with starch. The image analysis method may, thus, also be used for estimating the starch content, ash and fiber content.

TABLE II

Analysis of wheat flour particle analysis

TABLE II-continued

Analysis of wheat flour

| kernel fraction | % total surface | | | % of dry matter | | |
|---|---|---|---|---|---|---|
| | hull | aleurone | starchy endosperm | ash | fiber | starch |
| hull fraction | 55.0 | 11.4 | 33.6 | 3.8 | 14.2 | 19.3 |
| aleurone fraction | 12.2 | 9.1 | 78.7 | 2.7 | 3.9 | 53.6 |
| flour fraction | 1.0 | 0.9 | 98.1 | 0.5 | 0.2 | 86.9 |

Correlation coefficients between different analysis parameters in mixture experiments with hull fraction, aleurone fraction and flour fraction

| x/y | ash | fiber | starch |
|---|---|---|---|
| hull | +0.89 | +0.99 | −0.95 |
| aleurone | +0.98 | +0.87 | −0.96 |
| starchy endosperm | −0.93 | −0.99 | +0.98 |

The number of particles fluorescing with different colors or wavelengths may also be calculated by means of equipment simpler than an image analyzer, in which microscope-connected photomultipliers or other detection surfaces sensitive to the fluorescences from the hull and aleurone particles, and sensitive to the reflection of excitation radiation from non-flourescing particles or particle parts are connected to the field of view of the microscope. This technique is known to persons skilled in the art, for which reason it will not be described in greater detail.

The seed component part fractions in accordance with the above were also irradiated with X-rays in order to ascertain the reaction of the component parts to X-ray radiation. It proved that the starchy endosperm fraction had a fluorescence maximum at 3310–3600 MeV, which agrees with the fluorescence of potassium on X-ray radiation; that the aleurone fraction had one fluorescence maximum at 2020–2140 MeV, which agrees with the fluorescence maximum of phosphorus on X-ray radiation, and one fluorescence maximum at 2300–2470 MeV, which closely agrees with the fluorescence maximum of sulfur on X-ray radiation, and that the hull fraction had a fluorescence maximum at 1740–1830 MeV, which closely agrees with the fluorescence maximum of silica on X-ray radiation. These X-ray fluorescences are characteristic for starchy endosperm parts (potassium), aleurone parts (phosphorus, sulfur) and hull parts (silica).

An apparatus according to the invention for good manual estimation of the contents, of seed or kernel fraction samples, of hull layer parts, aleurone layer parts and starchy endosperm parts is shown in FIG. 7. This apparatus comprises a box 1 with a curtained opening 2 in in one side wall and a peep sight 3 in the top wall. Adjacent the peep sight 3, on either side thereof, are disposed spectral lamps 4, 5 and 6, respectively, of 330 nm, 450 nm and incandescence. One or more incandescent light tubes 7 are disposed under a partition 8 placed opposite the top wall. The center portion of the partition consists of an opal glass disk 9 which may be used as a receptacle surface for a sample and thus is permeable to the light tube light for illumination right through the sample, which may be advantageous. The intensity and activation/deactivation of these lamps and tubes are controlled each by means of a regulator 10 disposed on the outside of the box and connected to the lamps and tubes in a manner which is not shown in great detail.

Different emission filters 11 for the visible fluorescence from the starchy endosperm, aleurone and hull particles and particle parts are provided, these filters being selected on the basis of the spectrofluorimeter experiments and correlated to the maximum sensitivity of the eye for each respective fluorescence. The filters may, by means of rotary filter holders 12 located outside the box 1, be brought into alignment with the peep sight 3 so that the filter is located between the peep sight and the opal glass disk 9. A magnifying glass 13 is provided and may be maneuvred from outside the box into the path of the light from the sample. A brown color scale 14 having a field with increasing brown color intensity, a yellow fluorescence scale 15 having a field with increasing yellow/yellow-green color intensity and a blue fluorescence scale 16 having a field with increasing blue color intensity are disposed about the glass disk 9. The field of the color scale 14 is calibrated against known weight or volume proportions between hull parts and the other seed component parts in samples, the calibration being based on eye observations in visible light. The fields of the color scales 15 and 16 are calibrated against known weight or volume proportions between aleurone parts and hull parts in ground seed samples, these calibrations being based on, for example, prior image analyses and microscope observations in accordance with the description above.

The apparatus functions as follows: a ground seed fraction sample is manually introduced through the opening 2 and may be observed in the hand or placed on the glass disk 9 alternatingly under 350 nm excitation, 450 nm excitation and white light. The magnifying glass 13 may be moved in front of the peep sight 3 through which the sample may be observed under magnification. The obtained intensive fluorescence colors, and, if desired the visible brown color under incandescent light, are compared with the color scales 15, 16 and 14, respectively, for obtaining an estimation of the amount of aleurone layer component parts, hull layer component parts, and thereby also the amount of starchy endosperm component parts in the sample. By variation of the light setting from beneath and above the sample, it is possible conclusively to identify the botanical composition of the particles with respect to these component parts. The peep sight 3 or some other opening in the top wall of the box 1 may be disposed for mounting a camera.

Figure 8:
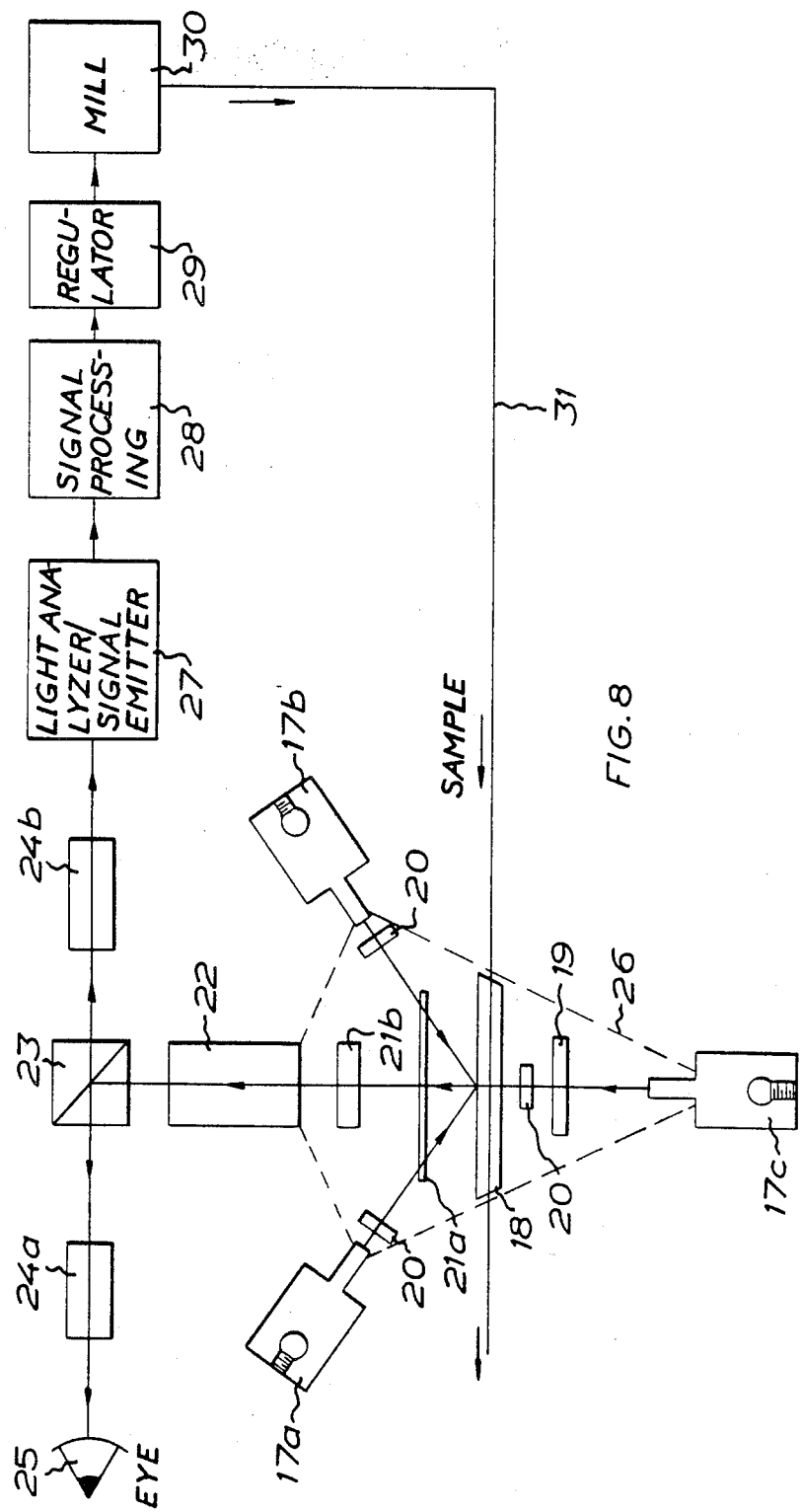
FIG. 8 is a schematic illustration of another apparatus according to the invention suitable for the automatic control of a mill process.

An apparatus for the automatic operational control of an installation for the separation of botanical component parts, such as a mill, is illustrated in FIG. 8. In this apparatus, a sample placed on a sample receptacle 18 is illuminated by means of a UV-lamp 17a or a lamp for visible light 17b and/or a lamp for incandescent light 17c. The lamps 17a and 17b are disposed for irradiation of the sample with incident light for fluorescence excitation of the sample, whereas the lamp 17c is disposed for illumination right through the sample, for which purpose the sample receptacle 18 is permeable to white light. A condenser 19 is disposed in front of the lamp 17c and a filter holder 20 is disposed in front of each lamp 17a–17c. Different filters may be inserted into these filter holders. The filters in front of the lamps 17a and 17b are selected in view of the fluorescences which are characteristic for the seed component parts in the sample. A quartz glass 21a is disposed above the sample receptacle 18 for allowing the passage of UV-light. A further filter holder 21b is disposed above the sample receptacle 18. A lens 22 receives the light which is let through or emitted by the sample in the sample receptacle, only that light being received since a screen 26 screens off light from outside. The light from the lens is led to an adjustable prism 23 which deflects a portion of the light to an occular 24a through which the eye 25 may observe the light from the sample, and another portion of the light to a second occular 24b which leads this portion of the light to a registration instrument or a light analyzer unit 27, such as an image analyzer, a spectrofluorimeter or a spectrophotometer or photomultipliers/light-sensitive detection surfaces. A signal processing unit 28 receives the signals issued from the unit 27 in dependence upon the content of the seed component parts in the sample and actuates, via suitable regulator devices or relays 29, the devices or means of the mill 30 for adjusting the grinding fineness and fraction composition, such as the nip adjustment means of the mill rollers or grinding disks, the sieves, the wind sieve fans etc. The signals from the unit 27 may also be utilized for transferring, via a shunt, an adulterated seed fraction, which adulteration may be discovered with the previously described means, to a special silo instead of to the silo provided for accommodating the pure or relatively pure fraction. The sample receptacle 18 may be disposed on or consist of a movable conveyor belt 32 which receives the samples from the mill for continuous analysis. Furthermore, the signal from the signal processing unit 28 may be utilized to order the introduction of a special sieve in the mill process, this sieve sifting off the impurities or adulterations. The signals from the unit 28 may also be used for automatic registration, calculation and printing-out of the composition of ground seed products for the automatic provision of a goods declaration on the packaging of these products.

Thus, the present invention has provided a method and an apparatus for identification of the botanical seed component parts: the hull layer, aleurone layer and starchy endosperm, which identification can, according to the invention, be utilized for both qualitative and quantitative analysis of ground seed samples. The identification and analysis carried out according to the invention has no destructive effect on the samples and entails no addition of chemicals to the samples, so that the analyzed samples may be returned to the mill process or packaging process. It should, here, be observed that the identification and analysis of the above-described botanical seed component parts; the hull layer, aleurone layer and starchy endosperm; have been given merely for purposes of exemplification: the method and apparatus according to the invention may be applied in association with separation processes for other botanical plant parts or other plant component parts and in conjunction with the identification of other botanical plant parts or other plant component parts for purposes other than separation.

We claim:

1. A method of identifying the proportions of starchy endosperm parts, aleurone layer parts and hull layer parts in a product produced by the disintegration of seeds having such parts comprising the steps of
   irradiating the product with electromagnetic radiation in a wavelength band of about 250 to about 300 nm to excite said starchy endosperm part of said product to fluoresce, electromagnetic radiation in a wavelength band of about 300 to about 370 nm to excite said aleurone layer parts of said product to fluoresce, and electromagnetic radiation in a wavelength band of about 410 to about 490 nm to excite said hull layer parts of said product to fluoresce, and analyzing the resulting fluorescence emitted by said product to identify relative starchy endosperm, aleurone layer, and hull layer proportions in said product.

2. A method as claimed in claim 1 further comprising actuating a nip adjustment means of a millroller to optimize the proportions of said parts in said product in response to the analysis of said resulting fluorescence.

3. A method as claimed in claim 1 further comprising actuating a nip adjustment means of a grinding disc to optimize the proportions of said parts in said product in response to the analysis of said resulting fluorescence.

4. A method as claimed in claim 1 further comprising actuating sieving devices to optimize the proportions of said parts in said product in response to the analysis of said resulting fluorescence.

5. A method as claimed in claim 1 further comprising actuating wind sieve fans to optimize the proportions of said parts in said product in response to the analysis of said resulting fluorescence.

6. A method as claimed in claim 1 further comprising transferring product containing an adulterated seed fraction to an alternate product silo in response to the analysis of said resulting fluorescence.

7. A method as claimed in claim 1 further comprising introducing a sieve into a mill process to sift off impurities or adulterations in said product in response to analysis of said resulting fluorescence.

8. A method as claimed in claim 1 further comprising using the results of said fluorescence analysis to register, calculate and print out the composition of said product.

9. A method as recited in any one of claims 1-8, wherein the irradiation is effected at such a wavelength band as excites the starchy endosperm parts of seeds to fluoresce in the proximity of 330 nm.

10. A method as recited in any one of claims 1-8, wherein the irradiation is carried out at such a wavelength band as excites the aleurone layer parts of seeds to fluoresce in the proximity of 425 nm.

11. A method as recited in any one of claims 1-8, wherein the irradiation is carried out at such a wavelength band as excites the aleurone layer parts of seeds to fluoresce in the proximity of 470 nm.

12. A method as recited in any one of claims 1-8, wherein the irradiation is carried out at such a wavelength band as excites the hull layer parts of seeds to fluoresce in the proximity of 520 nm.

13. A method as recited in any one of claims 1-8, wherein the emitted characteristic fluorescence is determined by means of a spectrofluorimeter and the intensity of the obtained fluorescence is measured by means of a spectrofluorimeter for determining the content of the component parts in the product.

14. A method as recited in any one of claims 1-8, wherein the irradiated product is analyzed in an image analyzer for determining the surface areas of the component parts by planimetry with the assistance of their characteristic fluorescences, and thereby, for determining the content of the component parts in the product.

15. A method as recited in any one of claims 1-8, wherein the results of said fluorescence analysis is converted to a signal indicative of the contents of said product and the signal is used for controlling a process for the disintegration of seeds.

16. A method as recited in claim 13, wherein the characteristic fluorescence determined by means of the spectrofluorimeter is utilized for selecting emission filters correlated to the maximum sensitivity of the human eye for the characteristic fluorescence.

17. A method of identifying the proportions of starchy endosperm parts, aleurone layer parts, and hull layer parts in a product produced by the disintegration of seeds having such parts comprising the steps of
   irradiating the product with fluorescence-imparting X-ray radiation and analyzing the resulting fluorescence emitted by said product in the range of about 1740 to about 3600 MeV to identify relative starchy endosperm, aleurone layer, and hull layer proportions in said product.

18. A method as recited in claim 17, wherein said X-ray radiation is selected for obtaining fluorescence emission from potassium in the starchy endosperm parts of seeds.

19. A method as recited in claim 17, wherein said X-ray radiation is selected for obtaining fluorescence emission from phosphorus in the aleurone layer parts of seeds.

20. A method as claimed in claim 17, wherein said X-ray radiation is selected for obtaining fluorescence emission from sulfur in the aleurone layer parts of seeds.

21. A method as recited in claim 17, wherein said X-ray radiation is selected for obtaining fluorescence emission from silica in the hull layer parts of seeds.

22. A method as recited in any one of claims 17 to 21, wherein the emitted characteristic fluorescence is determined by means of an X-ray fluorescence spectrometer, and the intensity of the obtained fluorescences is measured by means of an X-ray fluorescence spectrometer for determining the content of the component parts in the product.

23. A method of identifying in a sample of a product produced by the disintegration of seeds having starchy endosperm part, an aleurone layer part and a hull layer part the proportion of said sample which is starchy endosperm comprising the steps of
   irradiating the sample with electromagnetic radiation in a wavelength band of about 250 to about 300 nm to excite said starchy endosperm in the sample to fluoresce, and
   measuring the resulting fluorescence emitted by the product to ascertain the proportion of said sample which is starchy endosperm.

* * * * *